(12) United States Patent
Nakamura

(10) Patent No.: US 6,905,699 B2
(45) Date of Patent: Jun. 14, 2005

(54) INSECTICIDES

(75) Inventor: Satoshi Nakamura, Takarazuka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 109 days.

(21) Appl. No.: 10/332,050

(22) PCT Filed: May 21, 2001

(86) PCT No.: PCT/JP01/04238

§ 371 (c)(1),
(2), (4) Date: Jan. 6, 2003

(87) PCT Pub. No.: WO02/03801

PCT Pub. Date: Jan. 17, 2002

(65) Prior Publication Data

US 2003/0181453 A1 Sep. 25, 2003

(30) Foreign Application Priority Data

Jul. 6, 2000 (JP) ........................ 2000-204791

(51) Int. Cl.⁷ .................. A01N 25/00; A01N 43/58
(52) U.S. Cl. .................. 424/405; 514/247; 514/345
(58) Field of Search .................. 424/405; 514/247, 514/345

(56) References Cited

U.S. PATENT DOCUMENTS 4,751,225 A  6/1988  Nishida et al.
4,877,787 A  10/1989 Taniguchi et al.

FOREIGN PATENT DOCUMENTS

| JP | 1-242507 A | 9/1989 |
|----|------------|--------|
| JP | 3-220177 A | 9/1991 |
| JP | 8-92014 A  | 4/1996 |
| WO | 97/40692   | * 11/1997 |

* cited by examiner

Primary Examiner—Neil S. Levy
(74) Attorney, Agent, or Firm—Birch, Stewart, Kolasch & Birch, LLP

(57) ABSTRACT

A pesticidal composition comprising 4-phenoxyphenyl 2-(2-pyridyloxy) propyl ether and 2-tert-butyl-5-(4-tert-butylbenzylthio) 4-chloropyridazin-3(2H)-one as active ingredients, and a method for controlling pests using 4-phenoxyphenyl 2-(2-pyridyloxy)propyl ether and 2-tert-butyl-5-(4-tert-butylbenzylthio)-4-chloropyridazin-3(2H)-one.

2 Claims, No Drawings

INSECTICIDES

TECHNICAL FIELD

The present invention relates to pesticidal composition.

BACKGROUND ARTS

It is known that 4-phenoxyphenyl 2-(2-pyridyloxy)propyl ether has a pesticidal activity in U.S. Pat. No. 4,751,225. It is also known that 2-tert-butyl-5-(4-tert-butylbenzylthio)-4-chloropyridazin-3(2H)-one has a pesticidal activity in U.S. Pat. No. 4,877,787.

However, the pesticidal activities of these compounds may be unsatisfactory in some cases and it is desired to be developed more excellent pesticidal composition.

DISCLOSURE OF THE INVENTION

According to the present invention, a pesticidal composition comprising 4-phenoxyphenyl 2-(2-pyridyloxy)propyl ether given by formula (1):

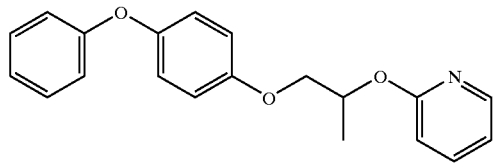

and 2-tert-butyl-5-(4-tert-butylbenzylthio)-4-chloropyridazin-3(2H)-one given by formula (2):

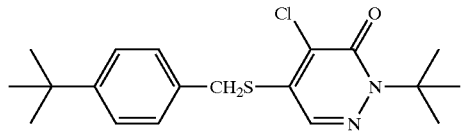

as active ingredients can be used for controlling pests which are difficult to control satisfactorily by each of the above compounds solely. Further, the pesticidal composition gives a synergistic action and the application dosages of these compounds can be decreased.

Namely, the present invention provides a pesticidal composition comprising 4-phenoxyphenyl 2-(2-pyridyloxy) propyl ether given by formula (1) (hereinafter, referred to as Compound A) and 2-tert-butyl-5-(4-tert-butylbenzylthio)-4-chloropyridazin-3(2H)-one given by formula (2) (hereinafter, referred to as Compound B) as active ingredients and a pesticidal method comprising applying an effective amount of 4-phenoxyphenyl 2-(2-pyridyloxy)propyl ether and 2-tert-butyl-5-(4-tert-butylbenzylthio)-4-chloropyridazin-3(2H)-one to pests or a place where the pests inhabit.

Compound A comprised in the pesticidal composition of the present invention can be manufactured according to the description of U.S. Pat. No. 4,751,225 and it is also available in the market. Compound B can be manufactured according to the description of U.S. Pat. No. 4,877,787 and it is also available in the market.

Examples of the pest controlled by the pesticidal composition of the present invention include the following arthropods such as insects and acarina and nematoda:

Hemipteran pests such as Delphacidae (planthoppers) [e.g. *Laodelphax striatellus* (small brown planthopper), *Nilaparvata lugens* (brown planthopper) and *Sogatella furcifera* (white-backed rice planthopper)], Deltocephalidae (leafhoppers) [e.g. *Nephotettix cincticeps* and *Nephotettix virescens*], Aphididae (aphids) [e.g. *Aphis gossypii* (cotton aphids), *Myzus persicae* (green peach aphid), *Aphis citricola, Lipaphis pserudobrassicae* (turnip aphid), *Nippolachnus piri, Toxoptera aurantii* (black citrus apid) and *Toxoptera ciidius* (brown citrus apid)], stink bugs [e.g. *Nezara antennata* (green stink bug), *Cletus punctiger, Riptortus clavetus* (bean bug) and *Plautia stali* (oriental stink bug)], Aleyrodidae (whiteflies) [e.g. *Trialeurodes vaporariorum* (greenhouse whitefly), *Bemisia tabaci* (sweetpotato whitefly) and *Bemisia argentifolli* (silverleaf whitefly)], scales [e.g. *Aonidiella aurantii* (California red scale), *Comstockaspis perniciosa* (San Jose scale), *Unaspis citri* (citrus snow scale), *Pseudaulacaspis pentagona* (white peach scale), *Saissetia oleae* (brown olive scale), *Lepidosaphes beekii* (purple scale), *Ceroplastes rubens* (red wax scale) and *Icerya purchasi* (cottonycushion scale)], Tingidae (lace bugs) and Psyllidae (suckers);

Lepidopteran pests such as Pyralidae [e.g. *Chilo suppressalis* (rice stem borer), *Cnaphalocrocis medinalis* (rice leafroller), *Ostrinia nubilalis* (European cornborer), *Parapediasia teterrella* (bluegrass webworm), *Notarcha derogata* (cotton leafroller) and *Plodia interpunctella* (Indian meal moth)], Noctuidae [e.g. *Spodoptera litura* (tobacco cutworm), *Pseudaletia separata* (rice armyworm), *Mamestra brassicae* (cabbage armyworm), *Agrotis ipsilon* (black cutworm), *Trichoplusia* spp., *Heliothis* spp. and *Helicoverpa* spp.], Pieridae [e.g. *Pieris rapae*], Tortricidae [e.g. *Adoxophyes* spp., *Grapholita molesta* (oriental fruit moth) and *Cydia pomonella*], Carposinidae [e.g. *Carposina niponensis* (peach fruit moth)], Lyonetiidae [e.g. *Lyonetia* spp.], Lymantriidae [e.g. *Lymantria* spp. and *Euproctis* spp.], Yponameutidae [e.g. *Plutella xylostella*], Gelechiidae [e.g. *Pectinophora gossypiella* (pink bollworm)], Arctiidae (tiger moths) [e.g. *Hyphantria cunea* (fall webworm)] and Tineidae [e.g. *Tinea translucens* (casemaking clothes moth) and *Tineola bisselliella* (webbing clothes moth)]; Dipteran pests such as *Culex* spp. [e.g. *Culex pipiens pallens* and *Culex tritaeniorhynchus*], *Aedes* spp. [e.g. *Aedes aegypti* and *Aedes albopictus*], *Anopheles* spp. [e.g. *Anopheles sinensis*], Chironomidae (midges), Muscidae [e.g. *Musca domestica* (housefly), *Muscina stabulans* (false housefly) and *Fannia* spp. (little house flies)], Calliphoridae, Sarcophagidae, Anthomyiidae [e.g. *Delia platura* (seedcorn maggot) and *Delia antiqua* (onion maggot)], Tephritidae (fruit flies), Drosophilidae (vinegar flies), Psychodidae (sand flies), Simuliidae (black flies), Tabanidae, Stomoxyidae (stable flies) and Agromyzidae (leafininer flies);

Coleopteran pests such as corn rootworms [e.g. *Diabrotica virgifera virgifera* (western corn rootworm) and *Diabrotica undecimpunctata howardi* (southern corn rootworm)], Scarabaeidae [e.g. *Anomala cuprea* and *Anomala rufocuprea*], Curculionidae (weevils) [e.g. *Sitophilus zeamais* (maize weevil), *Lissorhoptrus oryzophilus* (ricewater weevil), *Hypera pastica* (alfalfa weevil) and *Callosobruchuys chienensis* (adzuki bean weevil)], Tenebrionidae (darkling beetles) [e.g. *Tenebrio molitor* (yellow mealworm) and *Tribolium castaneum* (red flour beetle)], Chrysomelidae (leaf beetles) [e.g. *Aulacophora femoralis* (cucurbit leaf beetle), *Phyllotreta striolata*

(striped flea beetle) and *Leptinotarsa decemlineata* (Colorado beetle)], Anobiidae, *Epilachna* spp. [e.g. *Epilachna vigintioctopunctata*], Lyctidae (powderpost beetles), Bostrychidae, Cerambycidae and *Paederus fuscipes;*

Dictyopteran pests such as *Blattella germanica* (German cockroach), *Periplaneta fuliginosa* (smokybrown cockroach), *Periplaneta americana* (American cockroach), *Periplaneta brunnea* (brown cockroach) and *Blatta orientalis;*

Thysanopteran pests such as *Thrips palmi, Thrips tabaci, Thrips hawaiiensis* (flower thrips), *Scirtothrips dorsalis* (yellow tea thrips), *Frankliniella intonsa* (flower thrips), *Frankliniella occidentalis* (western flower thrips) and *Ponticulothrips diospyrosi;*

Hymenopteran pests such as Formicidae (ants), Vespidae (hornets), Bethylidae and Tenthredinidae (sawflies) [e.g. *Athalia japonica* (cabbage sawfly)];

Orthopteran pests such as Gryllotalpidae (mole crickets) and Acrididae (grasshoppers);

Siphonapteran pests such as *Ctenocephalides felis* (cat flea), *Ctenocephalides canis* (dog flea) and *Pulex irritans* (human flea);

Anopluran pests such as *Pediculus humanus corporis* and *Phthirus pubis* (crab louse);

Isopteran pests such as *Reticulitermes speratus* and *Coptotermes formosanus;*

Acarina such as Tetranychidae (spider mites) [e.g. *Tetranychus urticae* (two-spotted spider mite), *Tetranychus kanzawai* (Kanzawa spider mite), *Panonychus citri* (citrus red mite), *Panonychus ulmi* (European red mite) and *Oligonychus* spp.], Eriophyidae [e.g. *Aculops pelekassi* (pink citrus rust mite) and *Calacarus carinatus* (purple tea mite)], Tarsonemidae [e.g. *Polyphagotarsonemus latus*], Tenuipalpidae (false spider mites), Tuckerellidae, Ixodidae [e.g. *Haemaphysalis japonica* (Japanese tick), *Haemaphysalis flava* (yellow tick), *Haemaphysalis longicornis, Boophils microplus, Ixodes ovatus* and *Ixodes persulcatus*], Acaridae [e.g. *Tyrophagus putrescentiae* (copra mite)], Dermanyssidae [e.g. *Dermatophagoides farinae* (American house dust mite), *Dermatophagoides ptrenyssnus*], Cheyletidae [e.g. *Cheyletus eruditus, Cheyletus fortis, Cheyletus malaccensi* and *Cheyletus moorei*] and chicken mites]; and Nematoda such as *Pratylenchus coffeae* (coffee root-lesion nematode), *Pratylenchus fallax, Pratylenchus loosi, Pratylenchus vulnus* (walnut root-lesion nematode), *Heterodera glycines* (soybean cyst nematode), *Globodera rostochiensis* (potato cyst nematode), *Meloidogyne hapla* (northern root-knot nematode) and *Meloidogyne incognita* (southern root-knot nematode).

In the pesticidal composition of the present invention, the mixing ratio of Compound A to Compound B is usually 30:1 to 1:50, preferably 5:1 to 1:5, more preferably 4:1 to 1:2 by weight.

The pesticidal composition of the present invention may be a mixture of Compound A with Compound B as it is, but usually further comprises a solid carrier, liquid carrier, gaseous carrier and/or bait (base material for poison bait), optionally surfactant and other auxiliaries to be formulated to oil solution, emulsifiable concentrates, flowable, granules, dusts, aerosol, fogging, smoking, poison bait, microcapsule formulation, ULV formulation, spot-on formulation, pour-on formulation, shampoo formulation, sheet formulation and resin formulation.

These formulations usually contain 0.01 to 95% by weight for the total amount of Compound A and Compound B.

Examples of the solid carrier used for the formulation include fine powders and granules of clays such as kaolin clay, diatomaceous earth, synthetic hydrated silica, bentonite, Fubasami clay and terra alba; talc; ceramics; the other inorganic minerals such as sericite, quartz, sulfur, activated carbon, calcium carbonate and hydrated silica; and chemical fertilizers such as ammonium sulfate, ammonium phosphate, ammonium nitrate, urea and ammonium chloride. Examples of the liquid carriers include water; alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosene and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

Examples of the gaseous carrier include fluorocarbons, butane gas, LPG (liquefied petroleum gas), dimethyl ether and carbon dioxide.

Examples of the surfactant include alkyl sulfate ester salts, alkylsulfonate salts, alkylarylsulfonate salts, alkylaryl ethers and polyoxyethylenated derivatives thereof, polyethyleneglycol ethers, polyvalent alcohol esters and sugar alcohol derivatives.

Examples of the other auxiliaries such as adhesive agents, dispersants and stabilizers include casein; gelatin; saccharides such as starch, gum arabic, cellulose derivatives and alginic acid; lignin derivatives; bentonite; saccharides; synthetic water-soluble polymers such as polyvinyl alcohol, polyvinylpyrrolidone and polyacrylic acids; PAP (isopropyl acid phosphate); BHT (2,6-di-tert-butyl-4-methylphenol); BHA (mixture of 2-tert-butyl-4-methoxyphenol and 3-tert-butyl-4-methoxyphenol); vegetable oils; mineral oils; fatty acids and fatty acid esters.

Examples of the base materials for the poison bait include bait ingredients such as grain powders, vegetable oils, sugars and crystalline cellulose; antioxidants such as dibutylhydroxytoluene and nordihydroguaiaretic acid; preservatives such as dehydroacetic acid; substances for preventing erroneous eating from children and pets such as red pepper powder; and pest-attracting flavors such as cheese flavor, onion flavor and peanut oil.

The pesticidal composition of the present invention may be prepared by mixing a formulation of Compound A with a formulation of Compound B. Further, Compound A and Compound B can be mixed at the time of application.

In the present pesticidal method, the pesticidal composition of the present invention is usually utilized, but it is possible to apply Compound A or its formulation and Compound B or its formulation simultaneously without mixing in advance. At that time, the ratio of Compound A to Compound B is usually 30:1 to 1:50, preferably 4:1 to 1:2 by weight.

In case of controlling agricultural or forestry pests by the pesticidal composition of the present invention, the total application rate of Compound A and Compound B is usually 1 to 10000 g per 1 hectare. Emulsifiable concentrates, wettable powders and flowables and the like are usually diluted with water to make the concentration of the active ingredients 10 to 10000 ppm and applied. Granules, dusts and the like are usually applied as they are. These formulations can be applied directly to plants which are crops to be protected from pests, or applied to soil for controlling the pests inhabiting the soil. Further, sheet or string formulation of the present pesticidal composition can be coiled, set on the neighborhood of the plant or spread on the soil surface near the plant.

In case of controlling hygienically unfavorable pests by the pesticidal composition of the present invention, emulsifiable concentrates, wettable powders and flowables and the like are usually diluted with water to make the concentration of the active ingredients 0.01 to 10000 ppm and applied. Oil solution, aerosol, smoking, poison bait and the like are applied as they are.

The pesticidal composition of the present invention can be utilized for controlling ectoparasites of cattle such as oxen, sheep, goats and chickens and small animals such as dogs, cats, rats and mice. In that case, it can be applied to the animals by conventional veterinary methods. Typical methods for systemic control are application of tablet, mixing with feed, administration of suppository or injection (e.g., intramuscular, subcutaneous, intravenous, intraperitoneal). Non-systemic control methods are, for example, spraying oil solution or aqueous liquid formulation, pour-on or spot-on treatment, washing animals with shampoo formulation, putting resin formulation such as collar or ear-tag to the animal. In case of the application to the animal body, the dosage of the total amount of Compound A and Compound B is usually in the range of 0.1 to 1000 mg per 1 kg of the animal weight.

The amounts or concentrations for application may vary depending upon type of formulations, timing, places and methods of application, kinds of pests, degree of damage, and other factors; they can therefore be increased or decreased without limitation to the above ranges.

The pesticidal composition of the present invention can be used with the other insecticide, acaricide, nematocide, fungicide, herbicide, plant growth regulator, synergist, fertilizer, soil improving agent or animal food.

Examples of the insecticide, acaricide and nematocide include pyrethroid compounds such as permethrin, cypermethrin, fenvarelate, esfenvarelate, fenpropathrin, biphenthrin, deltamethrin, fluvalinate, flucythrinate, allethrin, d-allethrin, prallethrin, cyphenothrin, phenothrin, resmethrin, tefluthrin, empenthrin, acrinathrin, cyhalothrin, cyfluthrin, etofenprox, halfenprox, silafluofen, tralomethrin, cycloprothrin, esbiothrin, transfluthrin, terallethrin, imiprothrin and 1-ethynyl-2-fluoro-2-pentenyl 3-(2,2-dichlorovinyl)-2,2-dimethylcyclopropanecarboxylate; organophosphorus compounds such as cyanophos, fenthion, fenitrothion, parathion, methylparathion, pirimiphos-methyl, diazinon, isoxathion, pyridaphenthion, chlorpyrifos, chlorpyrifos-methyl, oxydeprofos, vamidothion, malathion, phenthoate, dimethoate, thiometon, disulfoton, phosalone, phosmet, methidathion, prothiofos, sulprofos, profenofos, azinphosmethyl, pyraclofos, salithion, tetrachlorvinphos, dichlorvos, monocrotophos, naled, dimethylvinphos, propaphos, acephate, metamidofos and ethion; carbamate compounds such as carbaryl, metolcarb, isoprocarb, fenobcarb, propoxur, XMC, ethiofencarb, bendiocarb, pyrimicarb, carbosulfan, carbofuran, benfuracarb, furathiocarb, methomyl, thiodicarb, oxamyl, alanycarb, metoxadiazone and fenothiocarb; neonicotinoids such as nitroiminoimidazolidine derivatives, nitrovinylidenediamine derivatives [e.g. N-[(6-chloro-3-pyridylmethyl)-N-ethyl-N'-methyl-2-nitrovinylidenediamine (common name: nitenpyram)], nitroguanidine derivatives, cyanoacetamidine derivatives [e.g. $N^1$-[(6-chloro-3-pyridyl)methyl]-$N^2$-cyano-$N^1$-methylacetamidine (common name: acetamiprid)], cyanoiminothiazolidine derivatives [e.g. 1-(2-chloro-5-pyridylmethyl)-2-cyanoiminothiazolidine (common name: thiacloprid)], nitroiminotetrahydro-1,3,5-oxadiazine derivatives [e.g. 3-[(2-chloro-5-thiazolyl)methyl]-5-methyl-4-nitroiminotetrahydro-1,3,5-oxadiazine (common name: thiamethoxam)], nitroiminohexahydro-1,3,5-triazine derivatives [e.g. 3,5-dimethyl-1-[(2-chloro-5-thiazolyl)methyl]-2-nitroiminohexahydro-1,3,5-triazine]; nereistoxin derivatives such as cartap, bensultap and thiocyclam; chlorinated hydrocarbon compounds such as benzoepin, dicofol and tetradifon; formamidine derivatives such as amitraz and chlordimeform; phenylpyrazole derivatives such as ethiprole; benzoylphenylurea compounds such as diflubenzuron, teflubenzuron, chlorfluazuron, flufenoxuron, triflumuron, hexaflumuron, lufenuron and novaluron; triazine derivatives such as cyromazine; thiadiazine derivatives such as buprofezine; juvenoid compounds such as methoprene, hydroprene, fenoxycarb and diofenolan; tebufenozide; methoxyfenozide; halofenozide; chromafenozide; chlorofenapir; phenisobromolate; quinomethionate; propargit; fenbutatin oxide; hexythiazox; etoxazole; clofentezine; fenpyroximate; tebufenpyrad; pyrimidifen; polynactin complex; milbemectin; avermectin; ivermectin and azadirachtin.

EXAMPLES

The present invention will be further illustrated by the following formulation examples and test example; however, the present invention is not limited to these examples.

Formulation Example 1
Emulsifiable Concentrate

Fifteen parts of Compound A, 5 parts of Compound B, 8 parts of polyoxyethylenealkyl aryl ether, 2 parts of sodium alkylarylsulfonate and 70 parts of xylene are uniformly mixed to give an emulsifiable concentrate.

Formulation Example 2
Wettable Powders

Ten parts of Compound A, 5 parts of Compound B, 3 parts of sodium alkylbenzenesulfonate, 3 parts of sodium ligninsulfonate and 79 parts of diatomaceous earth are uniformly mixed and pulverized with a jet air mill to give wettable powders.

Formulation Example 3
Dusts

One part of Compound A, 3 parts of Compound B, 46 parts of talc and 50 parts of clay are uniformly mixed and pulverized to give dusts.

Formulation Example 4
Flowable

Five parts of polyoxyethylene styryl phenyl ether sulfate, 20 parts of 1% aqueous solution of xanthan gum, 3 parts of smectite mineral and 57 parts of water are mixed, to which 5 parts of Compound A and 10 parts of Compound B are added, and the resultant mixture is well stirred and then wet pulverized in a sand mill to give a flowable.

Formulation Example 5
Microcapsule Formulation

Five parts of Compound A, 5 parts of Compound B, 10 parts of phenylxylylethane and 0.5 part of Sumidur L-75 (toluenediisocyanate produced by Sumika Bayer Urethane Co., Ltd.) are mixed, and the resultant mixture is then poured into 20 parts of 10% aqueous gum arabic solution, followed by stirring in a homomixer to give an emulsion having an average particle diameter of 20 μm. Two parts of ethylene glycol is added to the emulsion and the reaction is allowed to proceed in a water bath at 60° C. for 24 hours to give a microcapsule slurry. Separately, 0.2 part of xanthan gum and 1.0 part of Veegum R (aluminum magnesium silicate produced by Sanyo Chemical Industries, Ltd.) are dispersed in 56.3 parts of ion-exchanged water to give a thickner solution.

Finally, 42.5 parts of the above microcapsule slurry and 57.5 parts of the above thickner solution are mixed to give a 10% microcapsule formulation.

Formulation Example 6
Oil Solution

One-tenth (0.1) part of Compound A and 0.5 part of Compound B are dissolved in a mixture of 5 parts of xylene and 5 parts of trichloroethane, and the resultant solution is then mixed with 89.4 parts of deodorized kerosene to give an oil solution.

Formulation Example 7
Poison Bait

Five milligrams (5 mg) of Compound A and 5 mg of Compound B are dissolved in 0.5 ml of acetone, and the resultant solution is then uniformly mixed with 5 g of solid feed powder for animals (Breeding Solid Feed Powder CE-2 produced by Japan Clea Co., Ltd.). Air drying the mixture to remove the acetone gives a poison bait.

Formulation Example 8
Resin Formulation

One part of Compound A and 1 part of Compound B are kneaded with 98 parts of polyethylene resin (Sumikathene produced by Sumitomo Chemical Co., Ltd.) in a pressure kneaer, followed by pelletizing. The pellets are extruded at 160° C. to 180° C. with an inflation film making machine to give a film-shaped resin formulation with a thickness of 0.1 mm.

Formulation Example 9
Heating Smoke Formulation

Fifty milligrams (50 mg) of Compound A and 50 mg of Compound B are dissolved in a suitable amount of acetone. The resultant solution is then absorbed in a porous ceramic plate with a size of 4.0 cm×4.0 cm and 1.2 cm of thickness to give a heating smoke formulation.

The following test example show usefulness of the present composition for active ingredient of insecticidal/acaricidal composition.

Test Example 1
Insecticidal Test Against Silverleaf Whitefly (*Bemisia argentifolii*)

To each of an aqueous dilution in a designated concentration of an emulsifiable concentrate of Compound A (commercial name: Lano EC, manufactured by Sumitomo Chemical Co., Ltd.) and a flowable of Compound B (commercial name: Sanmite flowable, manufactured by Nissan Chemical Industries, Ltd.), and a mixture of the emulsifiable concentrate of Compound A in a designated concentration with the flowable of Compound B in a designated concentration, a spreading agent (Shin-Rino, manufactured by Nihon Nohyaku Co., Ltd.) was added to make the amount of the spreading agent to 1/3000 of volume to prepare a spray solution.

Cabbage seedlings planted in 3 ounces plastic cup were placed in a net cage containing many living silverleaf whiteflies for 24 hours, so that silverleaf whiteflies became parasitic on the cabbage seedlings. Each of the above-prepared test solutions was sprayed with a spray gun. The number of silverleaf whiteflies (i.e., the total number of adults and larvae) surviving on the cabbage seedlings was examined just before and after 9 days from the treatment. The test results are shown in table 1.

TABLE 1

| Test Compound | Concentration of Active ingredients (ppm) | Number of insects before treatment | Number of surviving insects after 9 days |
|---|---|---|---|
| Compound A | 50 | 59 | 30 |
| Compound B | 12.5 | 75 | 155 |
|  | 50 | 75 | 10 |
|  | 100 | 56 | 13 |
| Compound A + | 50 + 12.5 | 84 | 6 |
| Compound B | 50 + 50 | 88 | 0 |
|  | 50 + 100 | 93 | 0 |
| No treatment | — | 115 | 286 |

Industrial Applicability

The pesticidal composition of the present invention has an excellent pesticidal efficacy.

What is claimed is:

1. A method for controlling pests which comprises applying a synergistic effective amount of 4-phenoxyphenyl 2-(2-pyridyloxy)propyl ether and 2-tert-butyl-5-(4-tert-butylbenzylthio)-4-chloropyridazin-3(2H)-one to pests or a place where the pest inhabits.

2. A method for controlling pests according to claim 1, wherein the weight ratio of 4-phenoxyphenyl 2-(2-pyridyloxy)propyl ether and 2-tert-butyl-5-(4-tert-butylbenzyl-thio)-4-chloropyridazin-3(2H)-one is in the range of from 30:1 to 1:50.

* * * * *